United States Patent
Perkins et al.

(10) Patent No.: US 10,336,001 B2
(45) Date of Patent: Jul. 2, 2019

(54) END EFFECTOR FOR WOUND CLOSURE DEVICE

(71) Applicant: Ethicon, Inc., Somerville, NJ (US)

(72) Inventors: Jason T. Perkins, Easton, PA (US); Jesse G. Nawrocki, Annandale, NJ (US); Jason Huff, Collingswood, NJ (US); David C. Lindh, Sr., Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 430 days.

(21) Appl. No.: 14/845,402

(22) Filed: Sep. 4, 2015

(65) Prior Publication Data
US 2017/0065271 A1    Mar. 9, 2017

(51) Int. Cl.
A61B 17/04     (2006.01)
B29C 65/02     (2006.01)
A61B 17/06     (2006.01)
A61B 17/00     (2006.01)

(52) U.S. Cl.
CPC ........ B29C 65/02 (2013.01); A61B 17/06166 (2013.01); *A61B 2017/00526* (2013.01); *A61B 2017/06176* (2013.01)

(58) Field of Classification Search
CPC .............. A61B 17/06166; A61B 17/04; A61B 2017/06176; A61B 2017/00526
USPC .................................................. 606/228–232
See application file for complete search history.

(56) References Cited

U.S. PATENT DOCUMENTS

| 5,312,436 | A  | * | 5/1994  | Coffey ............... A61B 17/0469 |
|           |    |   |         |                            606/224 |
| 6,241,747 | B1 |   | 6/2001  | Ruff |
| 6,264,675 | B1 |   | 7/2001  | Brotz |
| 6,730,112 | B2 |   | 5/2004  | Levinson |
| 8,709,183 | B2 |   | 4/2014  | O'Neill |
| 9,307,966 | B2 |   | 4/2016  | Tegels |
| D780,918  | S  |   | 3/2017  | Perkins et al. |
| 2004/0220616 | A1 | * | 11/2004 | Bonutti ............. A61B 17/0487 |
|           |    |   |         |                            606/232 |
| 2005/0004576 | A1 |   | 1/2005  | Benderev |
| 2005/0267531 | A1 |   | 12/2005 | Ruff et al. |
| 2007/0257395 | A1 |   | 11/2007 | Lindh et al. |
| 2009/0248067 | A1 |   | 10/2009 | Maiorino |
| 2009/0248070 | A1 |   | 10/2009 | Kosa et al. |
| 2010/0063540 | A1 | * | 3/2010  | Maiorino ......... A61B 17/06166 |
|           |    |   |         |                            606/228 |
| 2010/0146770 | A1 |   | 6/2010  | Morency et al. |
| 2010/0298871 | A1 |   | 11/2010 | Ruff et al. |

(Continued)

FOREIGN PATENT DOCUMENTS

CA    2771656 A1    9/2012
EP    1321103       12/2008

(Continued)

OTHER PUBLICATIONS

European Search Report and Written Opinion dated Feb. 8, 2017 for Application No. EP16186949.0, 10 pgs.

(Continued)

*Primary Examiner* — Kathleen S Holwerda
(74) *Attorney, Agent, or Firm* — Frost Brown Todd LLC

(57) ABSTRACT

A suture device including an improved welded fixation device at its distal end, to provide improved holding strength during and after implantation of the suture in tissue.

19 Claims, 12 Drawing Sheets

(56) References Cited

U.S. PATENT DOCUMENTS

2011/0054523 A1    3/2011  O'Neill et al.
2013/0085525 A1    4/2013  Nawrocki et al.
2014/0236229 A1    8/2014  Longo et al.

FOREIGN PATENT DOCUMENTS

EP      2 305 130 A2      4/2011
EP      2 436 317 A2      4/2012
EP      2 505 142 A1     10/2012
WO   WO 2012/004758 A1    1/2012

OTHER PUBLICATIONS

International Search Report and Written Opinion dated May 10, 2016 for Application No. PCT/US2015/048460, 14 pgs.

* cited by examiner

END EFFECTOR FOR WOUND CLOSURE DEVICE

FIELD OF THE INVENTION

The present invention relates generally to the field of medical devices, and more particularly to barbed suture devices having improved end effectors.

BACKGROUND

Many wound and surgical incisions are closed using surgical sutures or some other surgical closure device. Self-retaining sutures, also known as barbed sutures, are well known and have gained attention for various medical applications. Typically, self-retaining sutures are constructed with a series of retainers (also known as "barbs" or "protrusions", used interchangeably herein) that extend outwardly from the suture, and function to increase the holding strength of the suture and/or eliminate the need for knot tying.

Some sutures and barbed sutures have been known to include end effectors at the distal end of the suture to provide a "stop" at the end that prevents the suture from being completely pulled through tissue, while also increasing the holding strength of the suture and eliminating the need to tie knots to secure the suture. End effectors include, for example, anchors, knots, tabs, loops, and the like. Conventional thinking dictates that the larger the surface area of the stop in a direction perpendicular to the direction of insertion of the suture, the more holding strength that will be achieved. However, there are practical limitations on size however, as end effectors with large thicknesses or other dimensions may be intolerable in surgical procedures and/or palpable and therefore undesirable. One suitable end effector is seen in U.S. Publication No. 2013/0085525. Despite this effective end effector, the present invention seeks to provide an improved end effector that not only provides increased stopping and holding power, but proves tolerable in surgical procedures.

SUMMARY

In one embodiment, the present invention includes a composite suture device, including: an elongated suture body having a proximal end and a distal end, with a body running along a central axis; a welded or bonded fixation tab secured to the distal end, the composite fixation tab including: a first layer having a top side and a bottom side with thickness therebetween, and a length running parallel to the central axis, and a width running perpendicular to the central axis; a second layer having a top side and a bottom side with thickness therebetween, and a length running parallel to the central axis, and a width running perpendicular to the central axis; where the bottom side of the second layer is welded to the top side of the first layer.

The invention also includes methods of using such suture devices.

In other embodiments, the invention includes a method of forming a suture device having a welded or bonded fixation tab, comprising the steps of: forming a suture device from a preform ribbon having a desired thickness configuration, wherein suture device includes proximal end and a distal end, with a body running along a central axis, and a fixation tab, the fixation tab including a top side and a bottom side, and having a length, width and thickness; applying an end attachment to top side of fixation tab, the end attachment being formed from same preform ribbon as suture device and the end attachment having a substantially similar length and width as the fixation tab; and welding fixation tab and end attachment to each other to form a composite fixation tab.

DETAILED DESCRIPTION

The present invention provides a wound closure device, which may be a self-retaining suture, which has a filamentary body having a proximal end and a distal end, a stop element at the distal end of the filamentary body. The suture may be formed by any suitable method, but preferably is compound profile punched from preformed ribbon or strip of material in a manner described in more detail in U.S. Patent Publication No. 2007/0257395, issued as U.S. Pat. No. 7,850,894 on Dec. 14, 2010, which is incorporated herein by reference in its entirety. In some embodiments, the stop element may be generally flat, and may have a rectangular or square-like shape, or in other embodiments it may take a more oval or circular shape. As used herein, the term "stop element" refers to a device at the trailing (or distal) end of the suture, and may also be termed an "anchor", or an "end effector". One type of end effector that may be useful in the present invention includes that described in U.S. Publication No. 2013/0085525, the entire contents of which are incorporated by reference herein. While the aforementioned end effector is useful, the present invention seeks to provide an improved end effector that gives enhanced stopping and holding power while avoiding intolerance and other issues during and after surgical procedures.

Figure 1:
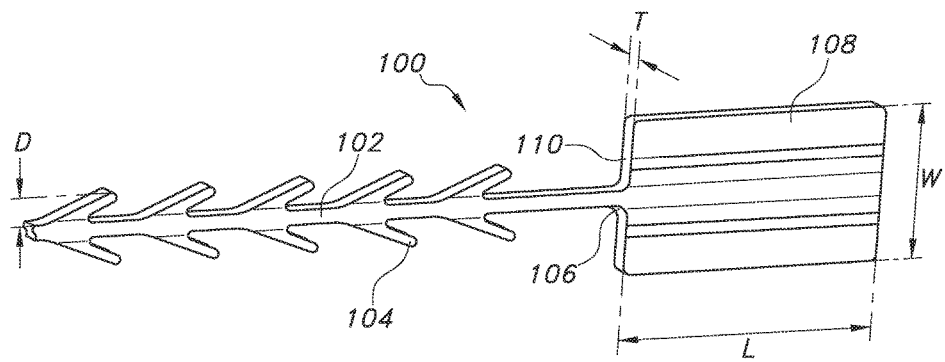
FIG. 1 shows a prior art suture device with a rectangular end effector.

FIG. 1 shows a prior art suture device 100 including an end effector 108, which is in the form of a tab (also referred to as a "fixation tab"), which is located at a distal end (106) of an elongated suture body 102. The suture body 102 has a longitudinal central axis between its distal end and an opposed proximal end (not seen), where the proximal end is an insertion end and may include a tissue penetrating feature, such as a needle. For self-retaining sutures, the body 102 may include a plurality of retainers 104, which may be arranged along the suture body 102 in any configuration, including, for example, symmetric, spiral, or in a random orientation.

As can be seen, the end effector 108 is generally rectangular, with an elongated length and width, with leading edge 110 defined by a leading edge thickness (t), a leading edge width (w), and also has a length (l). As used herein, and as seen in the Figure, the length of the end effector is parallel to the central longitudinal axis of the suture body 102. The width of the end effector 108 is substantially perpendicular to the central longitudinal axis of the filamentary element. In devices such as that seen in FIG. 1, the suture device 100 may be formed from a single preform or ribbon of suitable material, where the device 100 is die-cut or stamped or profile punched into the desired form. In such embodiments, the suture body 102 and the end effector 108 are stamped from the same preform, and therefore are a single unitary construction.

As used herein and throughout this application with reference to each of the components, the term "proximal" shall refer to the end of the suture device that is inserted into a tissue, while the term "distal" shall refer to the end of the suture device opposite the insertion end. In the suture device of FIG. 1, the distal end includes the end effector 108, and the insertion end (not shown) would be the furthest end along the suture body 102 that is opposed from the end effector 108. End effectors as described herein may also have a proximal end and a distal end, where the proximal end of the end effector is the location where the end effector is secured to the suture body 102 (e.g., at suture body distal end 106), and the distal end of the end effector is the opposed edge of the end effector along its length. The terms "distal" and "proximal" will generally refer to these ends of the suture device and/or the ends of the end effectors described herein.

Known sutures with end effectors such as that in FIG. 1 are typically stamped or formed from a single sheet of material, and therefore the thickness configuration of the end effector is the same as that of the suture body itself. That is, since the device is stamped from a single piece, the thickness configuration of the end effector 108 does not differ from the thickness configuration of the suture body 102. That is, the thickness of the suture body 102 is substantially similar to the thickness 110 of the end effector 108. In some embodiments, the central portion of the suture body (102) may have a different thickness than retainers 104, and this thickness variation may be similar along the length and width of the end effector 108. Thus, the end effector 108 may have a varying thickness configuration along its width, as may be seen in FIG. 2 and described below. Suitable end effectors need not be rectangular, but may be circular, oval, square, or other configurations. In some embodiments, the thickness (t) of the end effector of FIG. 1 may be approximately 8-25 mils, the width (w) may be approximately 70-120 mils, and the length (l) may be approximately 39-200 mils. The ratio of the length to the width of the stop element may be at least 1.5.

Prior devices such as that seen in FIG. 1 may include a pattern or other pre-formed configuration in the body of the end effector 108, which allows for the same pattern or pre-formed configuration to exist along the length of the suture body 102 through the end effector. For example, in FIG. 1, the thickness along the central axis of the suture body 102 is thicker in some points than in regions adjacent the central axis, such as the retainers 104, and this thickness variation is consistent along the length of the end effector 108.

Figure 2:
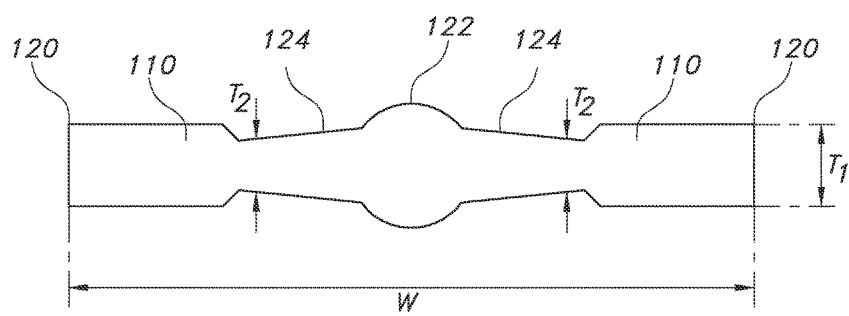
FIG. 2 shows a side view of the end effector of the suture of FIG. 1, as viewed along the central axis.

By way of example, prior end effectors may be formed from a single sheet of material, having a thickness of from about 6-25 mils, typically from 4-12 mils, with a maximum thickness along the central axis of the suture device (i.e., along the central axis of the suture body 102) and/or at first and/or second outer edges, with a minimum thickness at a location between the central axis and the first and/or second outer edges. FIG. 2 shows a close up view of the end effector of FIG. 1 as viewed along its length (i.e., so that the width and thickness can be seen). As can be seen, in this embodiment, central region 122 of the end effector extends along the central axis of the suture body 102, and the end effector also includes a first outer region 120, second outer region 120, first intervening region 124 having thickness $t_2$, and second intervening region 124 also having thickness $t_2$. Thicknesses of each outer region 120 need not be identical, and the thicknesses of the intervening regions 124 also need not be identical. The cross-sectional thickness configuration of the end effector 108 may differ from that seen, for example, the thickness may be substantially the same along the entire width of the end effector 108 if desired.

The holding strength of the end effector may be increased by increasing the dimensions of the end effector; however, there are practical and clinical limitations on the size and mass that can be implanted. For example, if the device is too small, it may provide low strength, but if it is too large, it may undesirably leave a large mass within the body of implantation. In addition, larger masses sometimes suffer from difficulties in manufacturing and providing sound structure. The present invention allows for improved holding strength while avoiding such limitations. Specifically, the present invention provides a welded end effector, where the overall mass of the welded end effector is about 1.1-3.0 times the mass of a tab end effector that is unmodified as seen in FIGS. 1-2, and more specifically about 1.5 to about 2.0 times; but the thickness of the welded end effector is only increased about 1.1 times to less than 2 times the thickness of the tab end effector that is unmodified as seen in FIGS. 1-2. In desired embodiments, the increase in mass (compared to the unmodified tab end effector) is greater than the increase in thickness as compared to the same unmodified tab end effector. The cross section of the unwelded tab as seen in FIG. 2 has a contoured shape, but the welded tab may have a substantially rectangular cross-sectional configuration. In some embodiments, the welded tab may have a different shape, which can be formed by a shaped die having any desired configuration. This will be further explained below.

The device 100 may be made of a polymeric, metallic or ceramic material that are absorbable or non-absorbable. In yet another embodiment, the device is made of a polymer material selected from the group consisting of absorbable and non-absorbable homopolymers, random copolymers, block copolymers or blends made from polydioxanone, polyglactin, polyglycolic acid, copolymers of glycolide, lactide, and/or caprolactone, polyoxaesters, poliglecaprone, polypropylene, polyethylene, polyvinylidene fluoride (PVDF), hexafluoropropylene, copolymers of vinylidene fluoride and hexafluoropropylene, polyesters, polyethylene terephthalate, polybutylene terephthalate, glycol-modified polyethylene terephthalate, polytetrafluoroethylene, fluoropolymers, thermoplastic elastomers, ionomers, copolymers of ethylene and methacrylic acid, polyamides, polytetramethylene oxide, polystyrene, polybutadiene, polybutylene, etc. including combinations and/or copolymers of absorbable and non-absorbable materials.

Figure 3A:
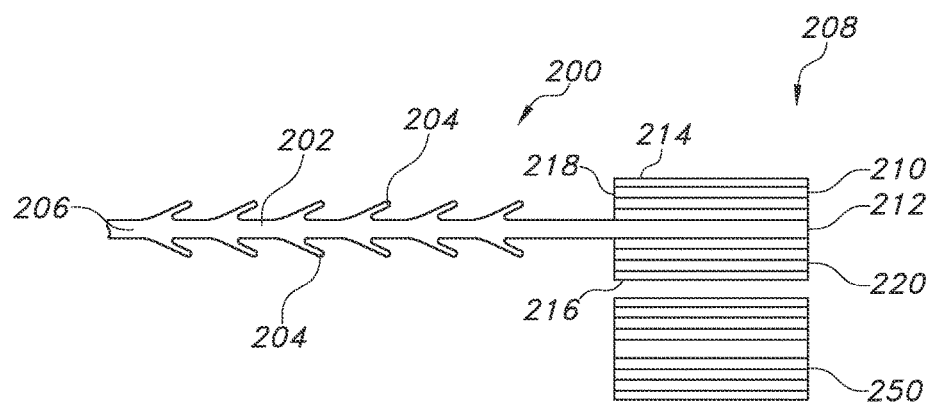
FIG. 3A shows a top view of a suture device with end effector and a separate end attachment in an unwelded configuration.

As can be seen in FIG. 3A, the present invention includes a suture device 200 having an elongated suture body 202, a plurality of retainers 204, the suture body being defined by a proximal (insertion) end 206 and a distal end 208. The device 200 includes an affixed end effector 210 at the distal end 208, which may be similar to that of FIG. 1. As can be seen, the end effector 210 of FIG. 3A includes a configuration having varying thicknesses across the width (w), and it may have the thickness configuration seen in FIG. 2. Of course, the end effector 210 may have a consistent thickness across its width if desired. The suture device 200 may be formed by stamping or profile punching the device from a single preform or ribbon of material, thereby ensuring that the suture body 202 and end effector 210 are formed of a unitary construction and include the same materials.

The present invention seeks to take this suture device 200, and modify its end effector 210 in various ways to increase its mass and holding strength, while avoiding complications associated with size increases of end effectors. FIGS. 3-11 show various configurations suitable to achieve this purpose. The composite device includes a suture having an end effector as described above, with a component welded or bonded to the end effector. In some embodiments, there is more than one end attachment welded to the end effector. The final device is a composite end effector (also referred to as a welded fixation tab or composite fixation tab), wherein the pieces are welded to each other, as will be described below. The composite fixation tab may refer to a "welded" fixation tab or a "bonded" fixation tab, and it should be understood that the composite fixation tab may include various components welded to each other (i.e., through application of energy), or may alternatively be bonded to each other, such as through application of chemical bonding or other known bonding techniques. Thus, the composite fixation tab may be bonded through chemical means or may be welded through application of energy.

A composite fixation tab has been shown to provide statistically significant gains in maximum load, elongation, and energy at break when compared to the fixation tab alone during tensile testing with a metal fixture. Importantly, however, the composite fixation tab does not increase the mass of the end effector to an undesirable level, and also does not introduce different materials to the device.

FIGS. 3A-3D describe one configuration using a single parallel welded attachment. FIG. 3A shows the suture body 200 described above, and a separate end attachment 250, which has a similar profile as the end effector 210 of the suture 200. As noted above, the device may be formed by cutting or stamping the suture and end effector from the same precursor material, referred to as a preform or a ribbon. Specifically, the end attachment 250 has a similar thickness configuration and a similar width as the end effector 210. The length may be different, or it may be the same. In the embodiment seen in FIG. 3A, the thickness of both the end effector 210 and the end attachment 250 has a separate thickness along the central region 212, the first outer region 214, the second outer region 216, the first intervening region 218 and second intervening region 220. The thickness of the central region 212 may be the same or may be different from the first outer region 214 and second outer region 216. The first outer region 214 may have the same thickness or a different thickness as the second outer region 216. The end attachment 250 in this embodiment should have a substantially similar thickness profile along its width as the end effector 210.

Figure 3B:
FIG. 3B shows a side view of the suture device of FIG. 3A with end attachment and end effector placed adjacent to each other.

As can be seen in FIG. 3B, one surface of the end attachment 250 is placed on one surface of the end effector 210, such that the width and length of each is substantially aligned with each other. It may be useful to use a method to maintain these components arranged with each other, such as a mechanical holding device and/or an adhesive or chemical securement. The maintenance of the components may be temporary, and allow for the two components to be secured to each other until welding is completed. In some embodiments, the multiple components may be held together in a die, both before and during the welding process. The die may be an RF die, including polymeric and/or metallic components.

It is particularly useful for the end attachment 250 to be cut or stamped from the same starting ribbon as the suture itself, to ensure that the width and thickness profile are substantially the same as the end effector 210. In addition, if the end attachment 250 is formed from the same ribbon as the suture 200 itself, the final composite material may be made from identical materials and specifically the same batch of polymeric material that is used to form the suture.

Figure 3C:
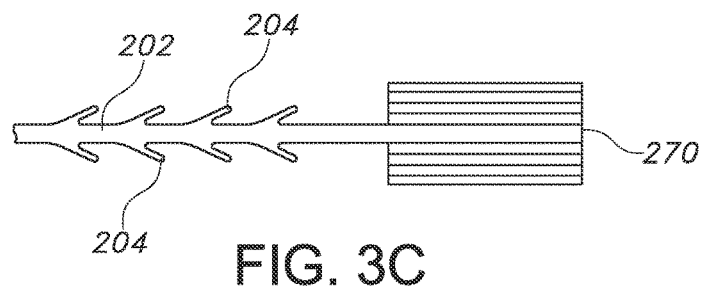
FIG. 3C shows a top view of the suture device of FIG. 3B after the end attachment and end effector are welded together.
Figure 3D:
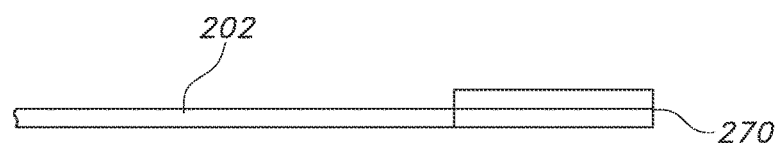
FIG. 3D shows a side view of the welded suture device of FIG. 3C.

Once the end effector 210 and the end attachment 250 are secured and held together, it is desirable to weld the components together to form the device as seen in FIG. 3C, where that the resulting composite fixation tab 270 is a secure composite device. In some embodiments, it is useful for the welding process to provide for a composite fixation tab 270 that has a substantially flat surface (the surface being defined by the length l and width w). In some embodiments, the resulting composite fixation tab 270 may have a similar thickness profile as the end effector 210 and end attachment 250 prior to welding. A view of the fixation tab 270 from the side (thereby depicting the thickness of the welded tab 270) can be seen in FIG. 3D. As can be seen, the thickness of the composite fixation tab 270 is only slightly larger than the thickness of the suture body 202. The thickness of the composite fixation tab 270 may be varied as desired. The composite fixation tab 270 may have a substantially rectangular cross section, or there may be any other desired shape, depending upon the shape of the die used. The sides and distal end of the composite fixation tab 270 may have a substantially flat surface, or there may be a seam where the end effector 210 and end attachment 250 were bonded together.

The welded tab 270 may be manufactured by welding or otherwise securing the end effector 210 and end attachment 250 to each other in any suitable fashion. For example, the devices may be secured to each other by welding with an RF generator. Other energy sources may be used to weld the devices together, including ultrasonic welding or thermal welding. Using an RF welder to add additional material to the tab has shown a 50-100% increase in tensile strength of the final composite fixation tab with a negligible addition of volume to the total device. While the mass of the tab will necessarily increase as more material is added to the device, the welding process evens out the profile of the fixation tab to give a uniform thickness that is only about 25-50% increase of the original thickness. Alternatively, chemical bonding may be used to secure the tab.

With proper die design and appropriate machine parameters, energy can be applied to the end effector 210 while leaving the rest of the device, particularly the core of the suture body 102, and the suture segment immediately preceding the end effector (e.g., at distal end 208), unaffected. The suture core retains its original strength and properties, while the resulting welded fixation device can have a unique morphology that makes it more resistant to shear stresses. Unlike other common forms of welding (thermal, ultrasonic, solvent) RF energy is able to heat from the inside out, instead of from the exterior to the interior of the device. This is an advantage because the polymer on the surfaces of the separate parts can begin to melt and form a weld with minimal distortion of the rest of the orientation in the tab. Despite the improved results when RF energy is used, other energy sources are contemplated and may be useful in certain embodiments. For example, a weld using thermal energy is possible and would be able to fuse the parts together. This may be useful in certain situations, while in others, RF energy may be more desired.

Through the use of the same material and the same dimensions, including the same thickness configuration, the strength of the resultant welded end effector increases significantly without increasing the variability. The welded tab has a greater mass than the initial end effector, for example, if one end attachment is used, it has approximately twice the mass of the initial design. However, the resultant composite fixation tab 270 has a substantially similar length and width as the original end effector 210, with only approximately a 10% to about a 25% increase in maximum thickness. This relatively small increase in thickness and the maintenance of the sizes of the other dimensions is due to the fact that both the original end effector 210 and the end attachment 250 are made from the same preform material, thereby ensuring that each has a similar contoured surface configuration prior to welding. In addition to enhancing the strength of the resulting composite fixation tab 270, adding additional mass to the fixation device has shown the ability to normalize the fixation tab data. The nominal fixation tab strength values do not follow any known distribution making manufacturing controls more difficult. Welding of the end effector 210 with end attachment 250 enhances the weak parts of the tab enough that the device strength can be modeled with several distributions, including the normal distribution.

In addition to a minimal increase in volume, the manner in which extra material is added to the device also minimizes additional surface area added to the device. Adding a single additional layer to the end effector, for example, only increases the surface area of the device by about 0.3%. This minimal change in surface area is noteworthy because surface area is a key driver for the rate at which additives or coatings can diffuse through a polymeric article. By essentially maintaining the surface area of the final composite fixation tab 270 post-welding, it is likely that the dosing requirements for additives or coatings can be maintained from pre-welded to post-welded fixation devices. The similar surface area also means there is a reduction in the number of additional sites for bacterial colonization or a tissue reaction in vivo.

Figure 5A:
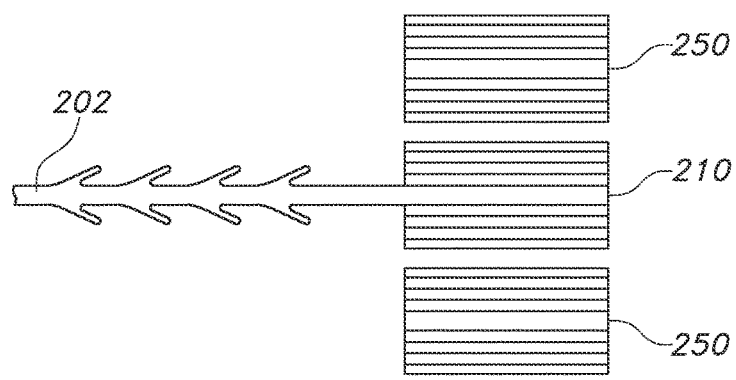
FIG. 5A shows a top view of a suture device with end effector and two separate end attachments, each having a parallel orientation, in an unwelded configuration.
Figure 5B:
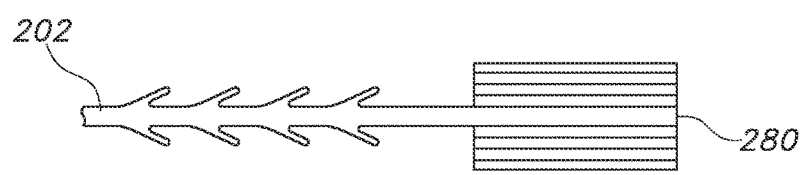
FIG. 5B shows a top view of the suture device of FIG. 5A after the end effector and end attachments have been welded together.
Figure 5C:
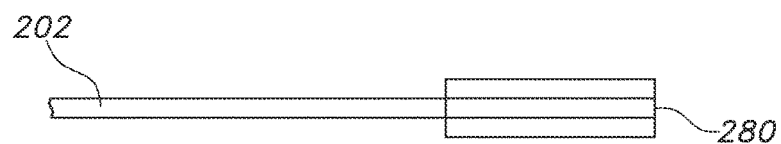
FIG. 5C shows a side view of the suture device of FIG. 5B.

The above welded tab design seen in FIG. 3 uses a single end attachment 250 secured to the end effector 210 in a parallel configuration. That is, the alignment of the molecules in each is aligned, and the thickness configuration in each is aligned as well. This parallel alignment gives the ability to utilize the orientation of the original end effector 210 and preform that existed before the weld, however, therefore multiple configurations and orientations are possible to increase the strength and performance of the tab in different manners. By arranging the preform in a parallel orientation, for example, the orientation in a given area across the width of the preform will increase as more of the same will be added on top of it. FIG. 5 shows a configuration using a double-parallel arrangement, whereby more than one end attachment is secured to the end effector, with each attachment being secured in a parallel configuration. As seen in FIG. 5A, the suture includes the preformed end effector, and a first end attachment 250 and second end attachment 250 are provided. The first and second end attachments 250 are secured to the end effector 210, either with the end effector 210 sandwiched between each end attachment 250, or with the end attachments 250 directly adjacent each other and the end effector 210 disposed outside of the two end attachments 250. FIGS. 5B and 5C show the welded configuration (in top down and from the side, respectively), with a welded fixation device 280 located at the distal end 208 of the suture device 200.

Figure 4A:
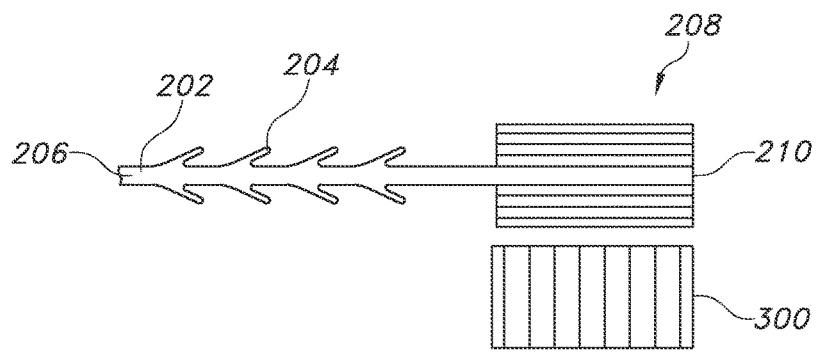
FIG. 4A shows a top view of a suture device with end effector and a separate end attachment having a perpendicular orientation, in an unwelded configuration.
Figure 4B:
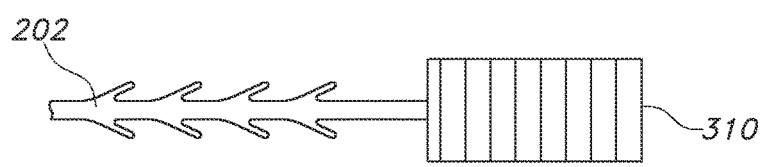
FIG. 4B shows a top view of the suture device of FIG. 4A after the end effector and end attachment have been welded together.
Figure 4C:
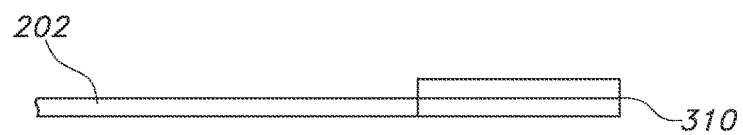
FIG. 4C shows a side view of the suture device of FIG. 4B.

Another possible arrangement is a perpendicular orientation as shown in FIG. 4, which uses the same mass of material as FIG. 3, but the end attachment 300 is cut such that the alignment of the material in the end attachment 300 is rotated approximately 90 degrees as compared to the end effector 210. The end attachment 300 still has approximately the same dimensional size and shape as the end effector 210 (e.g., approximately the same width, length and/or thickness), but with a different alignment of the molecules in the attachment. In addition, the thickness variation in the end effector 210 may be along its width, as seen in FIG. 2, while the thickness variation in the end attachment 300 may be along its length, as can be seen in FIG. 4A. The two components may be aligned and welded, as described above, and the resulting composite fixation tab 310 may be seen in FIGS. 4B and 4C. Thus, the composite fixation tab 310 includes a first side with a molecular orientation aligned in a first direction and a second side with a molecular orientation aligned in a perpendicular direction. The perpendicular orientation of the original end effector 210 and the end attachment 300 may result in an increased strength and stability of the final composite fixation tab 310, such as by ensuring that a crack or tear is not likely to propagate down the length or width of the composite fixation tab 310. Such cracks or tears are more likely to be arrested by the molecules arranged in the perpendicular direction.

Figure 6A:
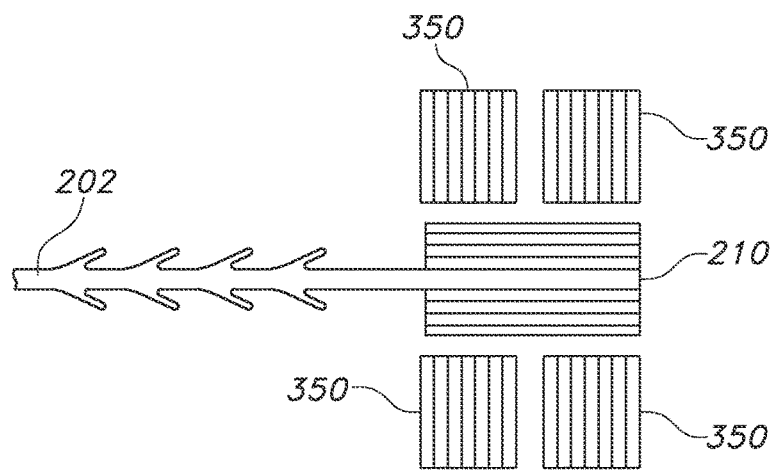
FIG. 6A shows a top view of a suture device with end effector and separate end attachments, each having a perpendicular orientation, in an unwelded configuration.
Figure 6B:
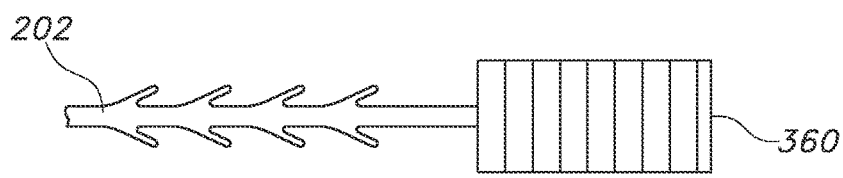
FIG. 6B shows a top view of the suture device of FIG. 6A after the end effector and end attachments have been welded together.
Figure 6C:
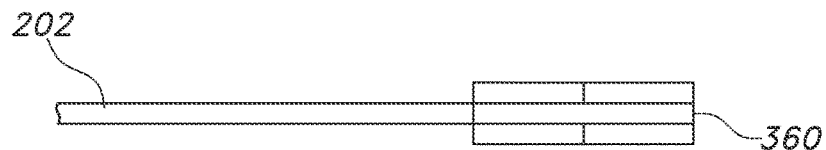
FIG. 6C shows a side view of the suture device of FIG. 6B.

In another perpendicular configuration, seen in FIG. 6, the original suture 200 with preformed end effector 210 is formed as described above, and an additional end attachment 350 is cut. However, in this embodiment, the end attachment is cut into multiple pieces (each 350). Each end attachment piece 350 may independently be parallel to the end effector 210 or may be perpendicular to the end effector 210. In the embodiment seen in FIG. 6A, four end attachment pieces 350 are formed, each being approximately half the length of the original end effector 210 and having approximately the same width as the end effector 210. This allows for each piece 350 to be placed and welded on the end effector 210 in desired locations. Here, two end attachment pieces 350 are welded onto a top surface of the end effector 210, and two end attachment pieces 350 are welded onto a bottom surface of the end effector 210. It may be desired for each end attachment piece 350 to be secured in a perpendicular configuration to the end effector 210, or with each end attachment piece 350 to be secured in a parallel configuration to the end effector 210, or combinations thereof. Each end attachment piece 350 is secured to the end effector 210 as described above, and subjected to welding as also described above. The resulting composite fixation tab 360 is seen in FIGS. 6B and 6C.

As can be seen in the various embodiments of FIGS. 3-6, the additional material to be welded to the end effector (210) can be formed, aligned and ultimately welded in a number of ways. Once the components are welded together, the resulting composite fixation tab is solid and secure, and the original components are not easily separated. As described above, in any of the above embodiments, the resulting composite fixation tab may have substantially flat surfaces, or they may have thickness variations as desired. FIGS. 3 and 4 describe methods of making composite fixation tabs through the addition of only one end attachment, while FIGS. 5 and 6 demonstrate that various layers and components may all be added to form the desired composite fixation tab. Each embodiment provides different strength profiles, ease of use and formation, and enhanced rigidity. Any of the embodiments seen in these Figures may be used depending upon the desired final composite fixation tab.

When only one end attachment is used, where the end attachment is approximately equal to the size and shape of the end effector, the resulting composite fixation tab has a mass that is approximately twice that of the original end effector prior to welding. In embodiments where two end attachments are used, where each end attachment is approximately equal to the size and shape of the end effector, the resulting composite fixation tab has a mass that is approximately three times that of the original end effector prior to welding. The composite may be a general sandwich configuration, where a first end attachment is placed on a top side of the end effector and a second end attachment is placed on a bottom side of the end effector.

Figure 7A:
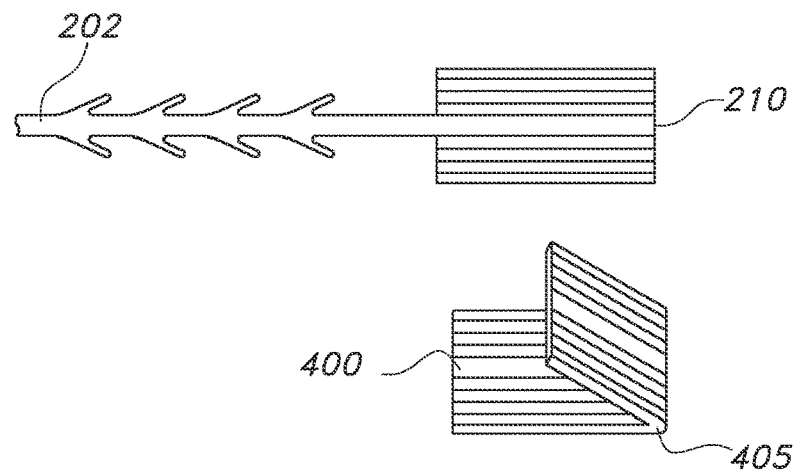
FIG. 7A shows a top view of a suture device with end effector and a separate foldable end attachment, in an unwelded configuration.
Figure 7B:
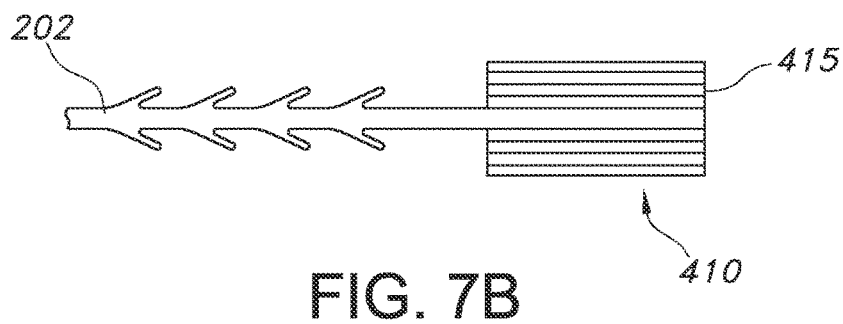
FIG. 7B shows a top view of the suture device of FIG. 7A after the end effector and foldable end attachment have been welded together.
Figure 7C:
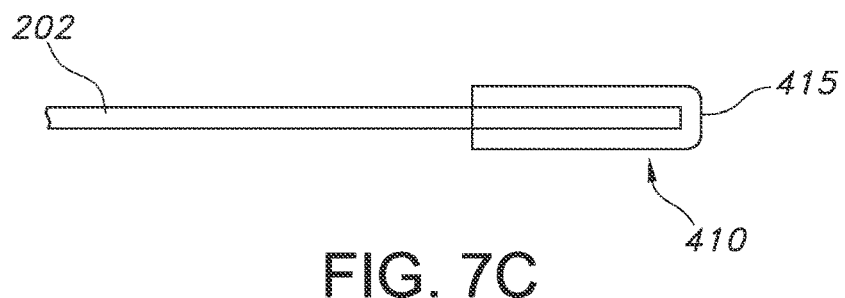
FIG. 7C shows a side view of the suture device of FIG. 7B.

An alternative method to forming a three-times mass composite fixation tab that does not incorporate an end effector and two separate end attachments (or more end attachments) may be seen in FIGS. 7A-7C. In this embodiment, the suture device 200 including end effector 210 is prepared as described above, and a separate end attachment 400 is formed, where the end attachment 400 is approximately twice the length of the end effector 210, and where the end attachment 400 is capable of being folded over itself along a line parallel to the width of the device. The device may include a folding region 405, as seen in FIG. 7A. The folded end attachment 400 can be disposed over the distal end of the end effector 210, held in place and ultimately welded in place, forming the composite fixation tab 410 as seen in FIGS. 7B and 7C. Composite fixation tab 410 includes welded fold region 415, which is the same region as fold region 405 after welding is complete. Desirably, the foldable end attachment 400 is sized and shaped such that, after folded over itself, the length and width of the folded device are approximately equal to that of the end effector 210. The resulting composite fixation tab 410 has a mass that is approximately three times that of the original end effector 210.

Figure 8A:
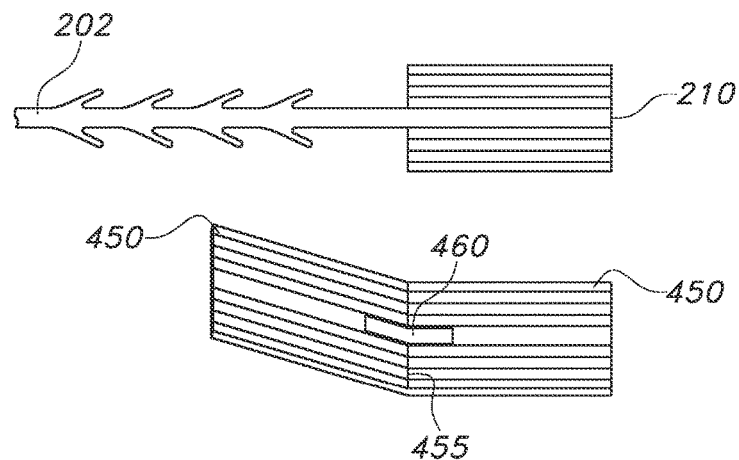
FIG. 8A shows a top view of a suture device with end effector and a separate foldable end attachment with central opening, in an unwelded configuration.
Figure 8B:
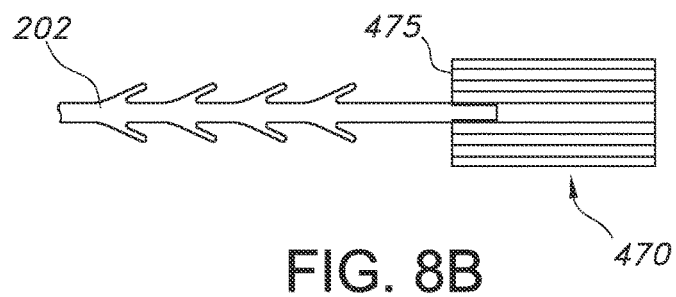
FIG. 8B shows a top view of the suture device of FIG. 8A after the end effector and end attachment have been welded together.
Figure 8C:
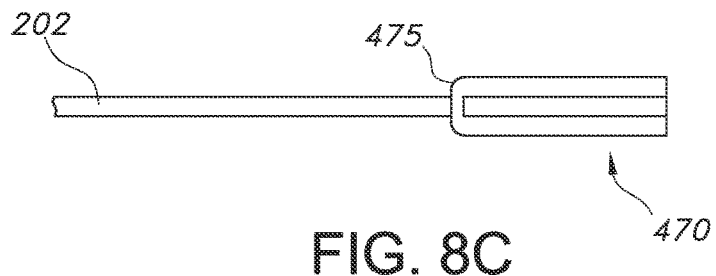
FIG. 8C shows a side view of the suture device of FIG. 8B.

Another embodiment of preparing an approximately three-times mass composite fixation tab can be seen in FIGS. 8A-8C. Again, the original suture 200 with end effector 210 is prepared, and a separate foldable end attachment 450 is also prepared, desirably from the same material and the same preform as the suture 200. The foldable end attachment 450 uses a substantially similar folded end attachment as seen in FIG. 7, where the foldable end attachment 450 includes a foldable region 455 along its width, but in this embodiment, a portion of the material from the middle of the end attachment 450 is removed (seen as region 460). With the removal of the middle portion at region 460, the foldable end attachment 450 may be slid over the proximal end 206 of the suture 200, and slid along the length of the suture body 202, where the foldable end attachment 450 aligns with the end effector 210. It may be desired or necessary to twist or rotate the foldable end attachment 450 prior to or during movement along the suture body 202. Once it has reached the end effector 210, it can be positioned to fold around the proximal end of the end effector 210. The device may be welded, forming the composite fixation tab 470 seen in FIGS. 8B and 8C. In this embodiment, the resulting composite fixation tab 470 includes a welded fold region 475 disposed at the proximal end of the composite fixation tab 470. As with FIG. 7, the welded fold region 475 is approximately at the same location as the fold region 460, but is welded. This configuration helps by further protecting the fixation tab 470 at its proximal end.

In the various embodiments described above, a separate component or components (i.e., the end attachment) is added to the end effector 210, and welded in place. An alternative to adding an additional material to the end effector is to slightly change the geometry of the end effector when it is initially formed, i.e., as it is stamped or punched, or by providing a device that includes a resulting composite fixation tab having a shorter length than the original end effector 210.

Figure 9A:
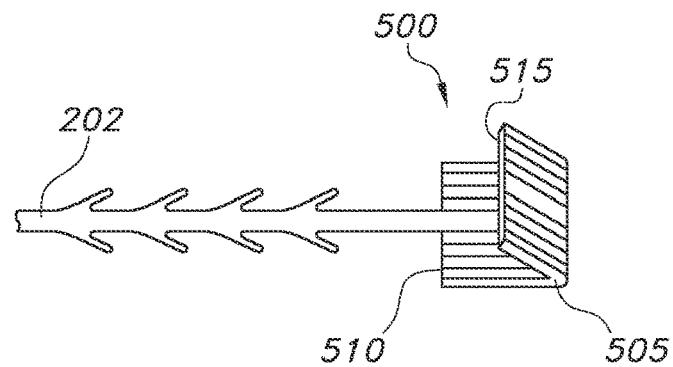
FIG. 9A shows a top view of a suture device with a foldable end effector, in an unwelded configuration.
Figure 9B:
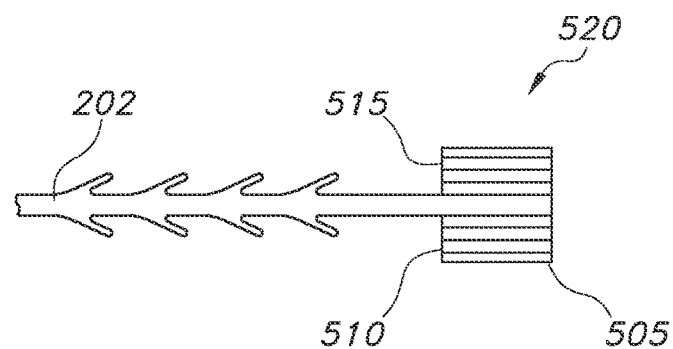
FIG. 9B shows a top view of the suture device of FIG. 9A after the end effector has been folded over itself and welded.
Figure 9C:
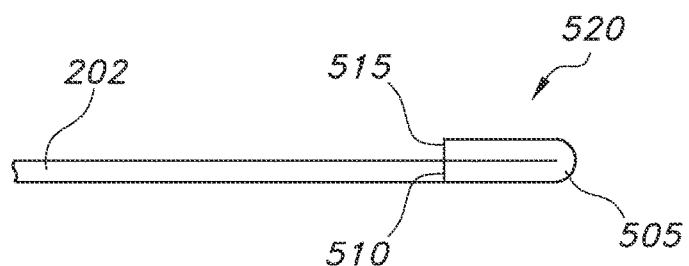
FIG. 9C shows a side view of the suture device of FIG. 9B.

For example, FIGS. 9A-9C show a device including the suture body 202 with an end effector 500. In this embodiment, the length of the end effector (as measured from proximal end 510 to distal end 515) is approximately twice the desired length of the final desired welded end effector, and is foldable along a fold region 505 extending along the width of the foldable end effector 500. In this embodiment, the foldable end effector 500 is folded in half, such that the proximal end 510 is substantially flush with the distal end 515 before welding. The folded end effector is then welded into place to form a welded fixation device 520 (FIG. 9B). A side view of this embodiment can be seen in FIG. 9C. This method has the advantage of avoiding the use of additional material or adding any additional components, which may differ from the end effector 500 material. In addition, this method avoids the need to secure separate pieces to each other. This also maintains the final, composite fixation tab 520 has a desired length that is equal to that of the original tab described above. In addition, the final welded fixation device 520 has the same mass of the device as originally formed.

Figure 10A:
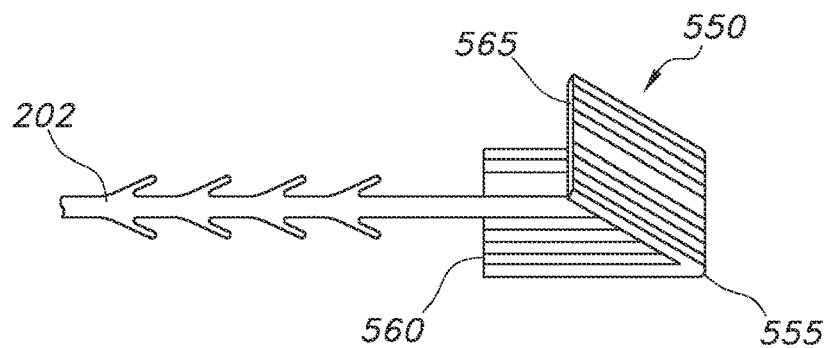
FIG. 10A shows a top view of a suture device with an elongated and foldable end effector, in an unwelded configuration.
Figure 10B:
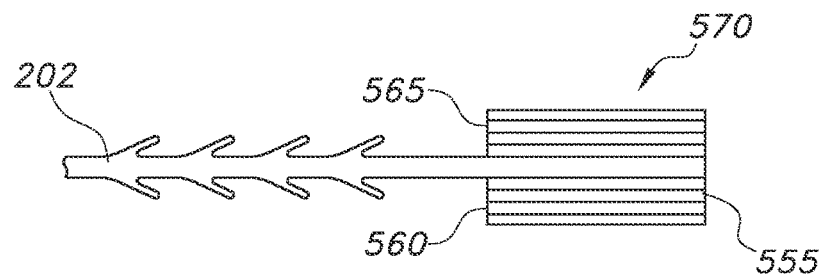
FIG. 10B shows a top view of the suture device of FIG. 10A after the end effector has been folded over itself and welded.
Figure 10C:
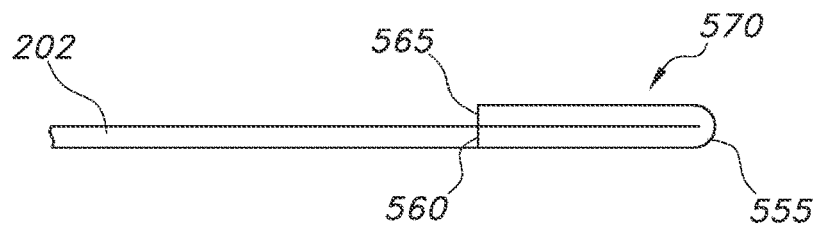
FIG. 10C shows a side view of the suture device of FIG. 10B.

In some embodiments, such as that seen in FIGS. 10A-10C, the end effector 550 has an elongated length as compared to prior devices (such as in FIG. 1), and is foldable along a fold region 555 extending across its width. In this embodiment, when the end effector 550 is folded over itself such that its proximal end 560 is substantially flush with the distal end 565, the resulting length of the welded end effector 570 is longer than that of the embodiment in FIG. 9. This embodiment will increase the thickness and make the welded fixation device 570 more rigid, but has a longer length than that of FIG. 9.

Figure 11A:
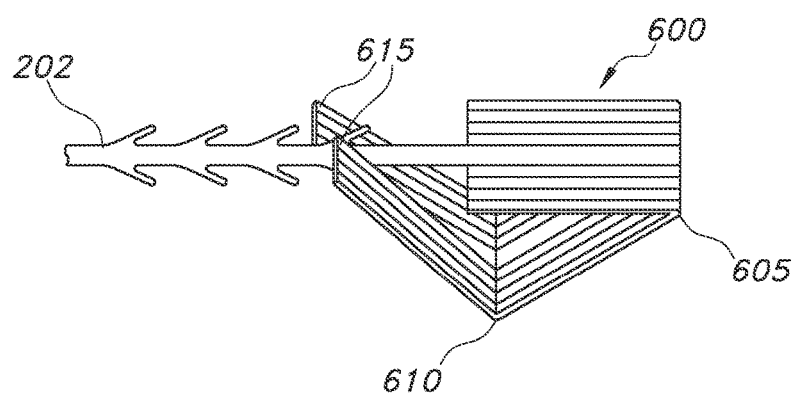
FIG. 11A shows a top view of a suture device with a foldable end effector having distal prongs, in an unwelded configuration.

In another embodiment, seen in FIGS. 11A-11-C, an end effector may be prepared that includes a two-fold design with prongs. In this embodiment, the end effector 600 includes an elongated length, with a first folded region 605 extending along its width, a second folded region 610 extending along its width at a different region, and first and second prongs 615 at the distal end of the end effector 600. The length of the first region (defined by the proximal end of the end effector 600 to the first folded region 605) is approximately equal to the length of the second region (defined as the length between the first folded region and the second folded region 610). The length of the prongs (defined as the length between the second folded region 610 and the distal end of the end effector 600) may be approximately equal the length of the first region and the second region.

Figure 11B:
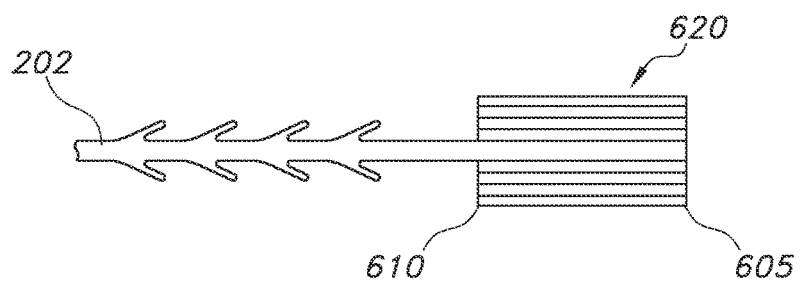
FIG. 11B shows a top view of the suture device of FIG. 11A after the end effector has been folded over itself and welded.
Figure 11C:
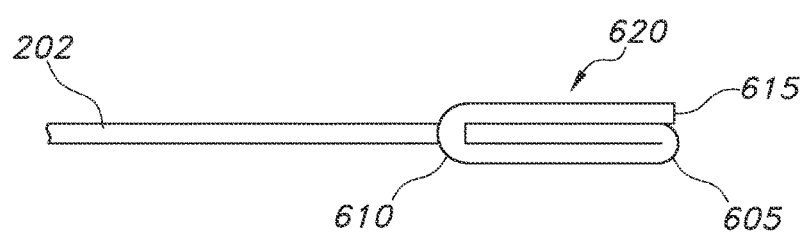
FIG. 11C shows a side view of the suture device of FIG. 11B.

In the embodiment of FIGS. 11A-11C, the end effector is initially stamped or punched from a preform, as explained in greater detail above, such that the length of the end effector 600 has approximately three times the length of the final desired welded fixation device. In this embodiment, there is an elongated region along a substantially central length removed from the most distal third of the end effector 600, forming first and second prongs 615. The amount of material removed to form the prongs 615 may vary, but it should be sufficient to allow the suture body 202 to pass through the space between the prongs 615. This extended prong shape allows the end effector to be folded over once (at the first folded region 605), then folded over again at the second fold region 610, where the prongs 615 may be passed over the suture body 202, and over the proximal end of the end effector 600 (Seen in FIG. 11A). The device may then be welded in place to form a welded fixation device 620, as seen in FIG. 11B, with a side profile seen in FIG. 11C. This design has similar advantages to the front fold around configuration seen in FIGS. 8A-8C, with in that the front face of the end effector 600 is enclosed and more resistant to cracking.

Each of the aforementioned configurations and methods result in a final, composite fixation tab that has a greater stability and effectiveness than an original stamped end effector, but does not significantly increase the thickness, width or length of the resulting welded end effector. In some embodiments, as described above, the mass may be doubled (if one end attachment is used, for example), or tripled (if two end attachments are used, for example), but the thickness of the end effector only increases by about 10% to about 70%, or about 25% to about 50%, depending upon the number of end attachments and size/shape/configuration of the end attachment(s). Further, the welding process may provide a composite fixation tab that has smooth surfaces of substantially similar thickness along the width of the final welded fixation device, and may include smooth edges and/or corners. Further, in some embodiments, molecular or physical alignment of the end effector with the end attachment(s) may be offset or may be perpendicularly arranged so as to provide a device with multiple molecular alignments. This may increase strength of the device.

In any of the aforementioned configurations, the welding of the resulting end effector is desirably achieved in a die that is suitably sized and shaped to provide the desired level of fixation and resulting shape. It is particularly desired that the die used be sized so as to snugly fit the various components within its welding space, and thereby allow the application of energy evenly to each of the surfaces of the composite device. The energy application should be sufficient to fuse the various attachment(s) to the original end effector, but not so much energy so as to melt the various components to the extent that their molecular orientation is substantially modified. When the components are melted to an undesirable level, the resulting welded end effector has less strength than desired. The resulting application of energy results in the attachment(s) and original end effector being fused to each other, with a visible seam about the periphery of the welded end effector. The fusion of the components should be sufficient to withstand the level of energy applied during normal surgical use without breaking or separating.

In use, the proximal end of a suture device including composite fixation tab is inserted through tissue until the suture has passed substantially through the tissue, and the proximal end of the composite fixation tab is abutting the outer surface of the tissue into which the device is implanted. The suture is prevented from being pulled through the tissue further by the abutment of the welded tab against the tissue surface. This holds the suture in place, and the user is able to continue suturing the tissue in desired regions of the body. If the suture includes a plurality of retainers along its body, as described above, these tissue retainers serve to hold the suture in place in the various regions of tissue into which the suture device is inserted. The combination of a composite fixation tab and plurality of retainers serves to prevent the suture from being pulled too far in the proximal direction, and simultaneously prevents or restricts removal of the device in the distal direction.

The resulting composite fixation tab provides a stronger and more secure stop at the distal end of the suture device, while avoiding problems, such as difficulties in manufacturing and difficulties post-implantation (such as when a device is used with too large of a mass remaining). Further, the resulting fixation device may include smoother and/or more uniform surfaces, allowing for ease of use and healing.

The present invention includes a method of suturing tissue through use of a suture including a welded fixation device. The suture may include a plurality of retainers along at least a portion of its body, where the retainers may be symmetrically disposed along the suture body, or they may be spirally wound about the suture body, or they may be randomly disposed about the suture body. Any of the welded fixation devices described above may be used as the welded fixation device at the distal end of the suture. The proximal end of the suture body should include an insertion means, such as a needle or other pointed end to be inserted through tissue. In use, a user, such as a doctor or other clinician, inserts the proximal end of the suture device into a desired location of tissue, pulling the suture body at least partially through the tissue. The retainers on the suture body allow for the suture to be pulled in the proximal direction, but restrict or otherwise slow down movement of the suture in the opposite (distal) direction. The proximal end of the suture is pulled through the tissue until the proximal end of the fixation device abuts the tissue into which the suture was inserted. At this point, the suture body is restricted from being pulled in the proximal direction further, and, with the presence of retainers on the suture body, the distal end of the suture is now held in place at the insertion site. The insertion end of the suture body may be inserted through a second region of tissue, either before or after the fixation device abuts the original region of tissue. The second region of tissue may be, for example, the side of a wound opposite the first tissue region. The user may continue to insert the proximal end of the suture device through as many regions of tissue as desired to effectuate wound closure.

In an alternative embodiment, there may be provided a bidirectional suture device with a central welded tab, which includes two sutures with unmodified tabs at their distal ends (as in FIGS. 1-2). In this embodiment, the unmodified tab of the first suture is rotated 180 degrees with respect to the unmodified tab of the second suture, such that the distal end of the first tab is substantially flush with the proximal end of the second tab. The first and second tabs may then be welded to each other, such as through RF welding or other application of energy. The resulting structure therefore includes a first suture with a proximal end facing in a direction opposite the proximal end of a second suture. Between the two proximal ends is a central welded tab. If desired, end attachments as described in any of FIGS. 3-11 may be used to provide additional mass to the central welded tab.

The suture, with welded fixation device, may be contained within a suitable package, such as a suture holder. Desirably, the suture is held in place in the package in such a fashion that the suture does not become entangled with itself during removal of the suture. It may be desired to wind the suture around one or more posts or other holding means within a suture package. The package should allow the user to grasp the proximal end of the suture, which may include a needle, and pull the suture proximally out of the suture package without restriction or entanglement. The suture may have a coating of an antimicrobial material contained thereon, which coating may be provided through any means, including dipping, spraying, vapor deposition, and the like. More than one suture may be contained within a package, or one suture may be contained within one package. The package may be hermetically sealed to protect the suture and maintain sterility of the suture.

EXAMPLES

Example 1

Benchtop Instron Testing

Tensile testing for each suture was conducted in a custom metal fixture via a benchtop Instron test, with a custom metal test fixture sized and shaped for the suture and/or the composite end effector. This test is more commonly referred to as a shear strength test, and for this example, it is considered a fixation tab shear strength test, since it measures the shear strength of the fixation tab(s) tested. The shear strength of each fixation tab was tested by loading each individual suture into the custom metal test fixture. Each test specimen was introduced into the slit in the fixture top plate such that the fixation tab was immediately in contact with the underside of the plate and the free end of the suture was available on the topside of the plate. The free end of the suture was gripped with the upper Instron grippers under light tension (enough to keep the suture taut) at a gauge length of 1 inch. The suture was aligned in the center of the grip such that it was perpendicular to the fixture and not angled. Each specimen was pulled at 12 in./min. to the point of fixation tab failure.

A suture was formed according to the design of FIG. 1, with a stamped end effector that was not manipulated after formation as the control ("nominal"). The control suture was a size 1 suture and was punched from PDS preform material, which is the in-process feedstock material used to make the suture. The tab end effector had a dimension of approximately 200 mils in length, approximately 95 mils in width, and approximately 19.5-21.5 mils in thickness, having the contoured profile seen in FIGS. 1-2. In addition, a second suture was formed of the same configuration, but a single parallel end attachment (described above and seen as FIGS. 3C-3D) was welded to the end effector via RF welding. The single parallel end attachment was formed by cutting from the same PDS preform material as used to form the control suture and the second suture into a substantially rectangular shape. This rectangular end attachment was welded onto the existing fixation tab of the second suture. The cut rectangular attachment had dimensions of approximately 200 mils in length, approximately 95-100 mils in width, and approximately 19.5-21.5 mils in thickness. The end attachment had the same contoured thickness profile as the unmodified tab, until the attachment and the tab were welded, at which time the welded end effector had a more rectangular cross sectional configuration. The shear strength of each fixation tab was tested by loading each individual suture into the custom metal test fixture. Each test specimen was introduced into the slit in the fixture top plate such that the fixation tab was immediately in contact with the underside of the plate and the free end of the suture was available on the topside of the plate.

The free end of the suture was gripped with the upper Instron grippers under light tension (enough to keep the suture taut) at a gauge length of 1 inch. The suture was aligned in the center of the grip such that it was perpendicular to the fixture and not angled. Each specimen was pulled at 12 in./min. to the point of fixation tab failure.

Table I shows the difference in performance between the nominal (unwelded, punched) tab and the RF welded tab (parallel configuration) of the same lot of material. Along with an increase in average strength, the lower values of the population are increased significantly, which translates to a decrease in the coefficient of variation. Less device variability translates to a more consistent product in the hands of a surgeon.

TABLE I

Strength Nominal vs RF Welded Fixation Tab.
n = 100 samples per group.

| | Mean (lbf) | StDev (lbf) | COV (%) | Min (lbf) | Median (lbf) | Max (lbf) |
|---|---|---|---|---|---|---|
| Fixation Tab (Nominal) | 6.233 | 1.223 | 19.65 | 3.3 | 6.475 | 8.99 |
| RF Welded Tab | 11.727 | 1.345 | 11.47 | 8.79 | 11.58 | 14.83 |
| % Increase Over Nominal | 88% | 10% | −42% | 166% | 79% | 65% |

Figure 12:
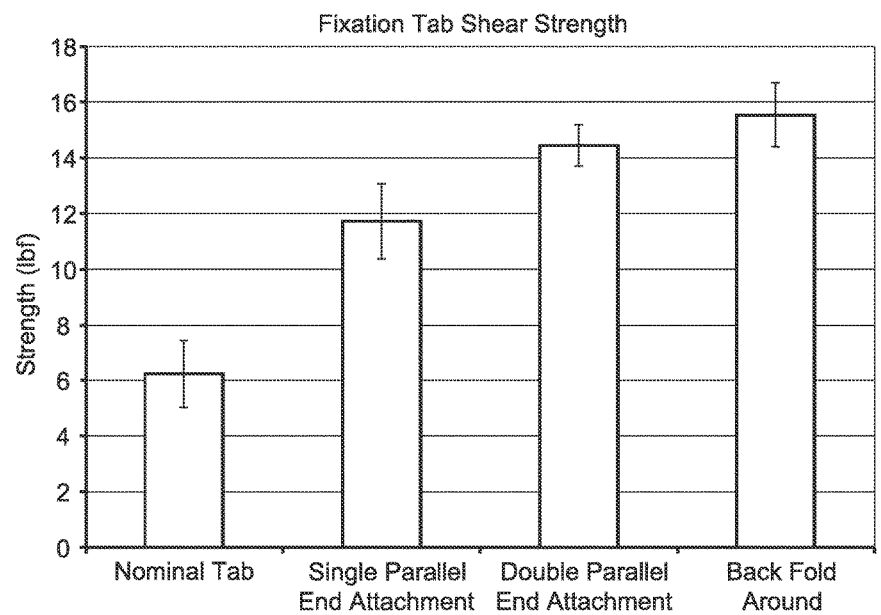
FIG. 12 shows a graph of the shear strength of various welded configurations.

FIG. 12 shows the tensile strength tested in a metal fixture of a nominal tabbed device (unwelded) as compared to various inventive embodiments. Inventive samples were prepared from the same lot of material as the nominal comparative device, with one formed as a parallel laminate, one formed as a double parallel laminate (FIGS. 5B-5C) and one as a folded attachment (FIGS. 7B-7C).

The % increase in average strength over the nominal (unwelded) fixation device for the 3 designs was 88% for a single parallel laminate end attachment, 132% for a double parallel laminate end attachment, and 149% for a back fold around end attachment.

Example 2

Porcine Initiation Strength Testing

Initiation strength is a different test than the shear strength test described in Example 1. During initiation strength testing, the suture device is inserted through porcine fascia tissue with the proximal end of the fixation tab abutted against the tissue and the free end of the suture loaded into an Instron for the pull to failure.

The comparative (nominal) suture was formed according to the design of FIG. 1 and as explained in Example 1, with a punched end effector that is not welded after formation. A second suture ("Inventive 1") was formed of the same material and size, but a single parallel end attachment (as in FIGS. 3C-3D) was welded to the end effector via RF welding (this configuration is explained as in Example 1). A third suture ("Inventive 2") was formed of the same material and size, but two substantially identical parallel end attachments were welded to the tab, one above the tab end effector and one below the tab end effector. The end attachments and the tab were aligned so as to be substantially flush with each other and each was welded to the end effector via RF welding concurrently. This configuration is referred to as a double parallel laminate design (as in FIGS. 5B-5C).

Figure 13:
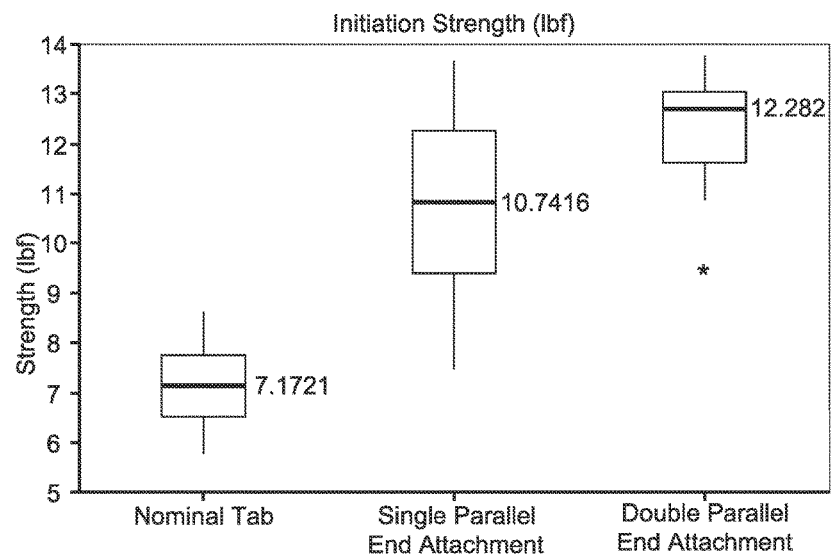
FIG. 13 shows a plot of initiation strength of various end effector configurations in porcine fascia.

The initiation strength testing measures the strength of the fixation device when implanted in porcine midline fascia. Each test specimen was prepared by first passing the proximal end of the suture through each side of an incision near the apex and pulling the suture through the fascia until the proximal end of the fixation tab is abutted against the porcine fascia tissue. The tissue specimen was placed in a raised fixture leaving the incision area exposed for visual observation and allowing the load to be applied to the proximal end of the suture (loaded perpendicular to the fixed tissue plane) until a device or tissue failure was noted by the test operator. This set-up simulates a surgeon pulling 'up' on the proximal suture end after initiation of the device into the tissue. As shown in FIG. 13, the inventive fixation devices provided an increase in the initiation strength relative to a nominal fixation device. The single parallel end attachment provided an approximately 50% increase over the nominal tab while the double parallel end attachment provided an approximately 70% increase over the nominal fixation tab.

Figure 14:
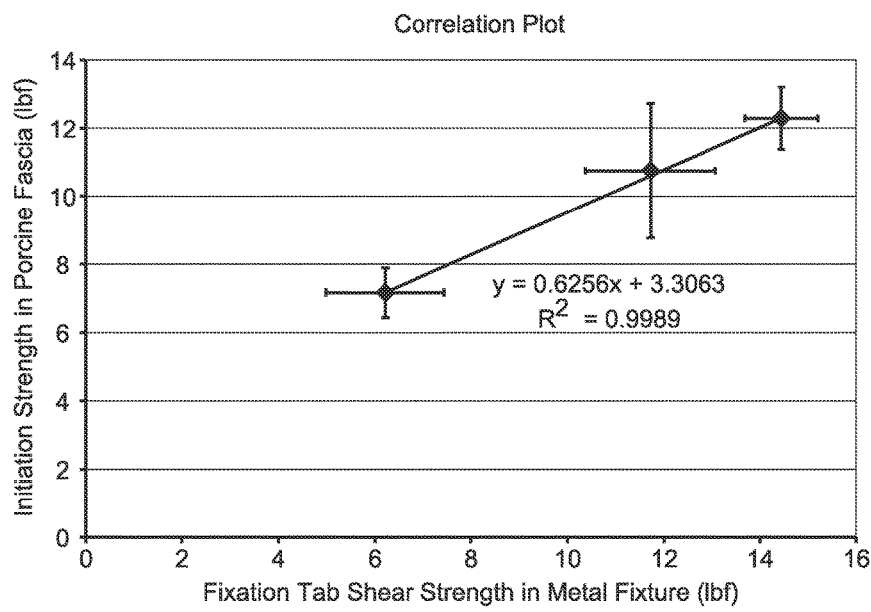
FIG. 14 shows a correlation plot of initiaition strength versus shear strength for multiple end effector configurations

FIG. 14 shows a correlation plot of initiation strength in porcine fascia (y axis) and the shear strength of the fixation device using the metal fixture (x axis) for the nominal fixation device, single parallel end attachment, and double parallel end attachment configurations. A linear fit of the data points results in an $R^2$ value of 0.9989 indicating a strong correlation between the two test methods.

What is claimed is:

1. A composite suture device, comprising:
   (a) an elongated suture body running along a central axis from a proximal end to a distal end, wherein the proximal end is free, wherein the elongated suture body includes a bottom side, a top side, and a first width running perpendicular to the central axis, wherein the elongated suture body has a first thickness; and
   (b) a composite fixation tab directly secured to said distal end, said composite fixation tab comprising:
       (i) a first layer having a top side, a bottom side, and the first thickness, wherein the first layer has a length running parallel to the central axis, and a second width running perpendicular to the central axis, wherein the first layer has two free ends running along the central axis; and
       (ii) a second layer having a top side and a bottom side with a thickness therebetween, and a length running parallel to the central axis, and a third width running perpendicular to the central axis, wherein the second layer has two free ends running along the central axis;
   wherein said bottom side of said second layer is welded to said top side of said first layer, wherein the second width and the third width are greater than the first width such that the first and second layers extend outwardly relative to the elongated suture body.

2. The composite suture device of claim 1, wherein said first and second layers have substantially the same width and length as each other.

3. The composite suture device of claim 1, wherein said first and second layers are made from the same material.

4. The composite suture device of claim 1, wherein the elongated suture body and the first layer are profile punched from a preform ribbon.

5. The composite suture device of claim 4, wherein said second layer is made from the same preform ribbon as the elongated suture body.

6. The composite suture device of claim 1, wherein said first layer has a thickness configuration, wherein said thickness configuration includes a thicker region at said central axis.

7. The composite suture device of claim 6, wherein said thickness configuration of the first layer includes a thicker region at a first and second side.

8. The composite suture device of claim 7, wherein the second layer has a substantially similar thickness configuration as the first layer.

9. The composite suture device of claim 1, wherein said elongated suture body has a plurality of retainers along its length, each of said retainers having a pointed end facing towards said distal end.

10. The composite suture device of claim 1, further including a third layer having a top side and a bottom side with a thickness therebetween, and a length running parallel to the central axis, and a width running perpendicular to the central axis.

11. The composite suture device of claim 10, wherein said third layer is welded to the bottom side of said first layer.

12. The composite suture device of claim 10, wherein the second layer and the third layer are secured to each other by folding an elongated element over itself.

13. The composite suture device of claim 1, wherein the first layer and the second layer have a perpendicular molecular alignment.

14. The composite suture device of claim 1, wherein the thickness of the composite fixation tab is about 1.1 to about 2.0 times the first thickness of the first layer prior to welding.

15. The composite suture device of claim 1, wherein the bottom side of the elongated suture body is coplanar with the bottom side of the first layer.

16. The composite suture device of claim 1, wherein the bottom side of the second layer is welded to the top side of the first layer throughout the entire lengths of the first and second layers.

17. The composite suture device of claim 1, wherein the first layer is integrally formed as a unitary piece together with the elongated suture body.

18. A composite suture device, comprising:
(a) an elongated suture body defining a longitudinal axis, wherein the elongated suture body has a first thickness; and
(b) a fixation tab attached to the elongated suture body, wherein the fixation tab comprises:
  (i) a first layer integrally attached to the elongated suture body and having the first thickness, and
  (ii) a second layer securely fastened to the first layer and having a second thickness;
wherein the first and second layers extend laterally relative to the longitudinal axis such that the fixation tab is wider than the elongated suture body, wherein the central axis of the elongated suture body passes through the center of the first layer, wherein one end of the elongated suture body is directly attached to the fixation tab and an opposing end of the elongated suture body is free, wherein a maximum thickness of the composite suture device is the sum of the first and second thicknesses.

19. A composite suture device, comprising:
(a) a planar suture body extending between a proximal portion and a distal portion, wherein the proximal portion is free;
(b) a planar end effector fixedly secured to the distal portion of the planar suture body, wherein the distal portion is disposed within a laterally central region of the planar end effector such that the planar end effector extends laterally outwardly from the planar suture body, wherein the planar end effector has a thickness that is the same as the planar suture body; and
(c) a planar end attachment positioned along the distal portion and the planar end effector, wherein the planar end attachment has a thickness, wherein the planar end attachment is welded to the distal portion and the planar end effector to thereby secure the planar end attachment to the planar suture body such that a maximum thickness of the composite suture device is the sum of the thicknesses of the planar end effector and the planar end attachment.

* * * * *